(12) United States Patent
Tomiyama et al.

(10) Patent No.: US 7,956,182 B2
(45) Date of Patent: Jun. 7, 2011

(54) PROCESS FOR PREPARING OPTICALLY ACTIVE ALCOHOLS

(75) Inventors: Hiroshi Tomiyama, Sakaki-machi (JP); Masayuki Yokota, Chikuma (JP)

(73) Assignee: Kotobuki Pharmaceutical Co., Ltd., Sakaki-machi, Hanishina-gun, Nagano (JP)

( * ) Notice: Subject to any disclaimer, the term of this patent is extended or adjusted under 35 U.S.C. 154(b) by 337 days.

(21) Appl. No.: 12/224,098

(22) PCT Filed: Feb. 13, 2007

(86) PCT No.: PCT/JP2007/052900
§ 371 (c)(1),
(2), (4) Date: Aug. 13, 2008

(87) PCT Pub. No.: WO2007/094480
PCT Pub. Date: Aug. 23, 2007

(65) Prior Publication Data
US 2009/0062527 A1 Mar. 5, 2009

(30) Foreign Application Priority Data
Feb. 16, 2006 (JP) .................... 2006-038964

(51) Int. Cl.
*C07C 29/143* (2006.01)
*C07C 33/22* (2006.01)
*C07C 67/31* (2006.01)
*C07C 69/65* (2006.01)
*C07C 205/08* (2006.01)
*C07B 53/00* (2006.01)
*C07B 61/00* (2006.01)
*C07D 263/14* (2006.01)

(52) U.S. Cl. .......... 540/200; 548/230; 560/60; 568/814
(58) Field of Classification Search .................. None
See application file for complete search history.

(56) References Cited

U.S. PATENT DOCUMENTS

| | | |
|---|---|---|
| 5,189,177 A | 2/1993 | Blacklock et al. |
| 5,618,707 A | 4/1997 | Homann et al. |
| 5,631,365 A | 5/1997 | Rosenblum et al. |
| 5,856,473 A | 1/1999 | Shankar |
| 5,886,171 A | 3/1999 | Wu et al. |
| 6,090,950 A * | 7/2000 | Heise ..................... 549/210 |
| 6,133,001 A | 10/2000 | Homann et al. |
| 6,207,822 B1 | 3/2001 | Thiruvengadam et al. |
| 6,218,585 B1 * | 4/2001 | Matos et al. ............. 568/814 |
| 6,627,757 B2 | 9/2003 | Fu et al. |
| 2007/0259845 A1 * | 11/2007 | Kansal et al. ........... 514/210.02 |

FOREIGN PATENT DOCUMENTS

| | | |
|---|---|---|
| WO | WO 00/34240 | 6/2000 |
| WO | WO 2005/066120 | 7/2005 |

OTHER PUBLICATIONS

Chen, Chinese Chemical Letters vol. 15, No. 2, pp. 167-168, 2004.*
A Novel One-Step Diastereo- and Enantioselective Formation of trans-Azetidinones and Its Application to the Total Synthesis of Cholesterol Absorption Inhibitors, by G. Wu et al, *J. Org. Chem.*, 1999, vol. 64, pp. 3714-3718.
Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption, by S. Rosenblum et al, *J. Med. Chem.*, 1998, vol. 41, pp. 973-980.
Process for preparing Ezetimibe intermediate by an acid enhanced chemo- and enantioselective CBS catalyzed ketone reduction, by X. Fu et al, Tetrahedron Letters, 2003, vol. 44, pp. 801-804.
Highly enantioselective reduction of achiral ketones with $NaBH_4$/$Me_3SiCl$ catalyzed by (S)-$\alpha,\alpha$-diphenylpyrrolidine-methanol, by B. Jiang et al, Tetrahedron Letters, 2000, vol. 41, pp. 10281-10283.

* cited by examiner

*Primary Examiner* — Mark Berch
(74) *Attorney, Agent, or Firm* — Flynn, Thiel, Boutell & Tanis, P.C.

(57) ABSTRACT

This invention relates to a process for producing optically active alcohols using asymmetric reduction of aromatic ketones. This process gives optically active alcohols in high enantioselectivity in a large scale production.

4 Claims, No Drawings

PROCESS FOR PREPARING OPTICALLY ACTIVE ALCOHOLS

TECHNICAL FIELD

This invention relates to a process for producing optically active alcohols using asymmetric reduction of aromatic ketones.

BACKGROUND TECHNOLOGY

Hydroxyalkyl substituted azetidinone derivatives, such as ezetimibe ([1-(4-fluorophenyl)-(3R)-[3-(4-fluorophenyl)-(3S)-hydroxypropyl]-(4S)-(4-hydroxyphenyl)azetidin-2-one]) represented by formula XII, are useful as hypochlesterolemic agents in the prevention and treatment of atherosclerosis.

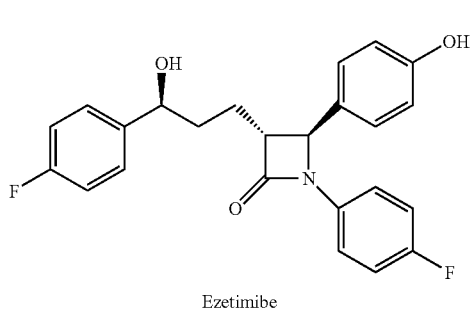

Ezetimibe (XII)

Several processes have been reported for the preparation of diphenylazetidinones. (Journal of Organic Chemistry, 1999, 64, 3714, Journal of Medicinal Chemistry, 1998, 41, 973, U.S. Pat. Nos. 5,631,365; 5,886,171; 6,207,822; 6,133,001; 5,856,473, WO2005/066120, JP 2002-531546, JP 2005-53931).

These processes involve that the β-lactam ring construction using 3-[(5S)-(4-fluorophenyl)-5-hydroxypentanoyl]-(4S)-phenyl-1,3-oxazolidin-2-one (VII) (method 1) or asymmetric reduction of derivatives having a carbonyl group in a side chain at the 3-position of a (3-lactam ring such as (4S)-(benzyloxyphenyl)-1-(4-fluorophenyl)-(3R)-[3-(4-fluorophenyl)-3-oxopropyl]azetidin-2-one (X) (method 2).

In Method 1, the intermediate, the hydroxyl group of 3-[(5S)-(4-fluorophenyl)-5-hydroxypentanoyl]-(4S)-phenyl-1,3-oxazolidin-2-one (VII) is protected with a suitable protecting group such as a trimethylsilyl or t-butyldimethylsilyl group, was used (U.S. Pat. No. 6,207,822, WO2005/066120, JP 2002-531546, JP2005-53931). 3-[(5S)-(4-fluorophenyl)-5-hydroxypentanoyl]-(4S)-phenyl-1,3-oxazolidin-2-one (VII) is synthesized by stereoselective microbial reduction of 3-[5-(4-fluorophenyl)-5-oxopentanoyl]-(4S)-phenyl-1,3-oxazolidin-2-one (VI) (U.S. Pat. No. 5,618,707).

It is reported that 3-[(5S)-(4-fluorophenyl)-5-hydroxypentanoyl]-(4S)-phenyl-1,3-oxazolidin-2-one (VII) is synthesized by asymmetric reduction of 3-[5-(4-fluorophenyl)-5-oxopentanoyl]-(4S)-phenyl-1,3-oxazolidin-2-one (VI) (U.S. Pat. Nos. 6,207,822; 6,627,757, Tetrahedron Letters, 2003, 44, 801.) These processes are a reduction by a borane-dimethylsulfide or borane-tetrahydrofuran complex using (R)-tetrahydro-1-methyl-3,3-diphenyl-1H,3H-pyrrolo(1,2-c)(1,2,3)-oxazaborolidine [(R)-MeCBS; XIII] as a catalyst to afford the corresponding alcohol in high enantioselectivity.

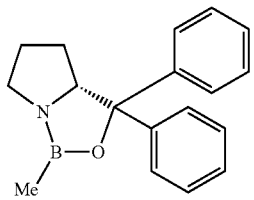

(XIII)

However, the enatioselectivity of the reduction depends on the rate and mode of addition of the borane-complex, moisture sensitivity of the reaction medium and the reaction temperature. Moreover, the reduction using a chiral catalyst leads to problems associated with the formation of over-reduced products, such as compound (XIV) (Tetrahedron Letters, 2003, 44, 801).

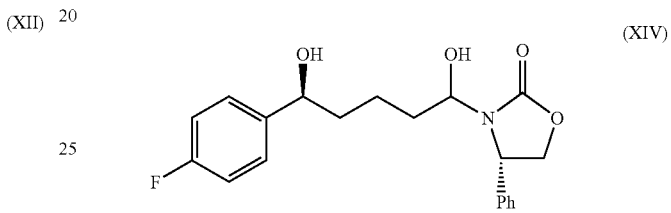

(XIV)

Borane-dimethylsulfide and borane-tetrahydrofuran-complex are expensive and toxic. Furthermore, the handling of these reagents is not easy in large production due to borane being a gas. (R)-MeCBS (XIII) is commercially available, but it is expensive. Moreover, a recycle process is required since (R)-2-(diphenylhydroxymethyl)pyrrolidine (XV), the product that (R)-MeCBS (XIII) is decomposed to by workup operations, is recovered. In this case, it is necessary that an expensive boron carrier, such as trimethylboroxine, be prepared (R)-MeCBS (XIII).

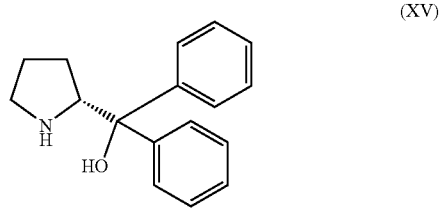

(XV)

WO2005/066120 discloses synthesis methods of 3-[(5S)-(4-fluorophenyl)-5-hydroxypentanoyl]-(4S)-phenyl-1,3-oxazolidin-2-one (VII) and (5S)-(4-fluorophenyl)-5-hydroxypentanoic acid methyl ester (IX) using (−)-B-chlorodiisopinocampheylborane (XVI) as a reducing agent.

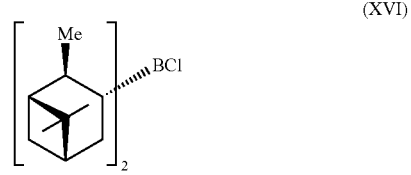

(XVI)

(5S)-5-(4-fluorophenyl)-5-hydroxypentanoic acid methyl ester (IX) is converted to 3-[(5S)-(4-fluorophenyl)-5-hydroxypentanoyl]-(4S)-phenyl-1,3-oxazolidin-2-one (VII) in this patent. This reaction also shows a high selectivity, however, a stoichiometric amount of reducing agent is necessary.

In method 2, (4S)-(4-benzyloxyphenyl)-1-(4-fluorophenyl)-(3R)-[(3S)-(4-fluorophenyl)-3-hydroxypropyl]azetidin-2-one (XI) is produced in high stereoselectivity by borane-complex asymmetric reduction of (4S)-(4-benzyloxyphenyl)-1-(4-fluorophenyl)-(3R)-[3-(4-fluorophenyl)-3-oxopropyl]azetidin-2-one (X) using (R)-MeCBS (XIII) as a catalyst. Compound (XI) is converted to ezetimibe (XII) by the removal of a benzyl group (Journal of Organic Chemistry, 1999, 64, 3714). However, this process also uses expensive (R)-MeCBS (XIII) and borane-complex.

The asymmetric reduction of aromatic ketones by sodium borohydride, chlorotrimethylsilane and a catalytic amount of optically active 2-diphenylhydroxymethyl)pyrrolidine (XV) system (Tetrahedron Letters, 2000, 41, 10281) has been reported. This reaction doesn't require a low reaction temperature. Furthermore, cheap and low toxic reagents are used in this reduction system. Moreover, 2-(diphenylhydroxymethyl)pyrrolidine (XV) is easily recovered during workup operations in a high yield, and recyclable after purification such as recrystallization. Reduction of 3-[5-(4-fluorophenyl)-5-oxopentanoyl]-(4S)-phenyl-1,3-oxazolidin-2-one (VI) by this system gives 3-[(5S)-(4-fluorophenyl)-5-hydroxypentanoyl]-(4S)-phenyl-1,3-oxazolidin-2-one (VIII) in a high yield and enantioselectivity [1 g scale ((R)-2-(diphenylhydroxymethyl)pyrrolidine 10 mol %): de 87%]. However, a tendency of decreased enantioselectivity of the product is observed at scale-up production (10 g scale ((R)-2-(diphenylhydroxymethyl)pyrrolidine 10 mol %): de 74%). Accordingly, the development of the catalyst, which shows a high enantioselectivity in large scale production, is desired.

DISCLOSURE OF INVENTION

This invention provides a synthesis method that shows a high enantioselectivity at large scale production of optically active alcohols by asymmetric reduction of aromatic ketones. In the course of study on the development of a enantioselective method of preparing optically active alcohols, the present inventors found that the use of optically active 2-[bis(4-methoxyphenyl)hydroxymethyl]pyrrolidine (IV) instead of optically active 2-(diphenylhydroxymethyl)pyrrolidine provides the alcohols in high enantioselectivity in a large scale production.

This invention relates to a process for producing optically active alcohols.

Namely, this invention provides a process that aromatic ketones represented by formula (I)

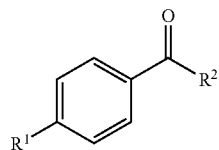

(I)

wherein $R^1$ is selected from a hydrogen atom, halogen atom, lower alkyl group (1 to 5 carbon atoms), lower haloalkyl group (1 to 5 carbon atoms), lower alkoxycarbonyl group (1 to 5 carbon atoms), lower alkoxy group (1 to 5 carbon atoms), hydroxyl group, nitro group, cyano group, lower acyoxy group (1 to 5 carbon atoms), lower alkylthio group (1 to 5 carbon atoms), lower alkylsulfonyl group (1 to 5 carbon atoms), substituted and unsubstituted amino group, substituted and unsubstituted carbamoyl group, substituted and unsubstituted aromatic ring or heteroaromatic ring. $R^2$ is —$(CH_2)n$-$R^3$, wherein n is 1 to 5 integer. $R^3$ is selected from a hydrogen atom, halogen atom, lower alkoxycarbonyl group (1 to 5 carbon atoms), lower alkoxy group (1 to 5 carbon atoms), lower alkylthio group (1 to 5 carbon atoms), lower alkylsulfonyl group (1 to 5 carbon atoms), substituted and unsubstituted amino group, unsubstituted carbamoyl group, substituted and unsubstituted aromatic ring or heteroaromatic ring and formula (II):

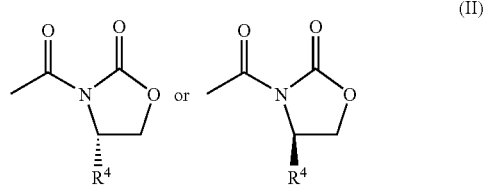

(II)

wherein $R^4$ is selected from a lower alkyl group (1 to 5 carbon atoms), substituted and unsubstituted aromatic ring, and substituted and unsubstituted benzyl group.

and formula (III):

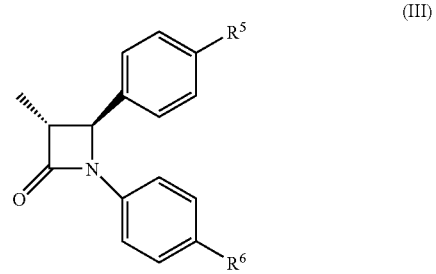

(III)

wherein $R^5$ and $R^6$ are the same or different and are selected from a hydrogen atom, halogen atom, lower alkyl group (1 to 5 carbon atoms), lower haloalkyl group (1 to 5 carbon atoms), lower alkoxycarbonyl group (1 to 5 carbon atoms), lower alkoxy group (1 to 5 carbon atoms), lower acyloxy group (1 to 5 carbon atoms), hydroxyl group, nitro group, cyano group, substituted and unsubstituted benzyl group, substituted silyl group, lower alkylthio group (1 to 5 carbon atoms), lower alkylsulfonyl group (1 to 5 carbon atoms), substituted and unsubstituted amino group, substituted and unsubstituted carbamoyl group, substituted and unsubstituted aromatic ring or heteroaromatic ring, substituted and unsubstituted tetrahydropyranyl group, lower alkyl group containing substituted and unsubstituted tetrahydropyranyl group (1 to 5 carbon atoms), lower alkyl group containing amino group (1 to 5 carbon atoms) are reduced by sodium borohydride, chlorotrimethylsilane and optically active 2-[bis(4-methoxyphenyl)hydroxymethyl]pyrrolidine represented by formula (IV)

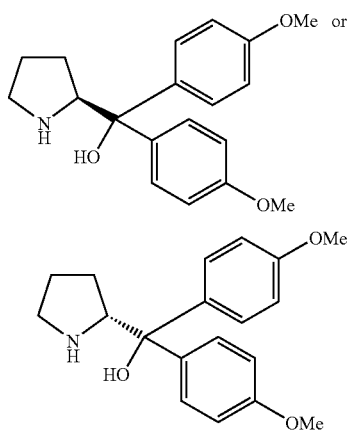

to give an optically active alcohol represented by formula (V) stereoselectively.

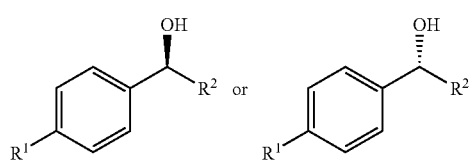

(wherein, R¹ and R² are as defined above.)

This invention also provides a process for 3-[5-(4-fluorophenyl)-5-oxopentanoyl]-(4S)-phenyl-1,3-oxazolidin-2-one represented by formula (VI)

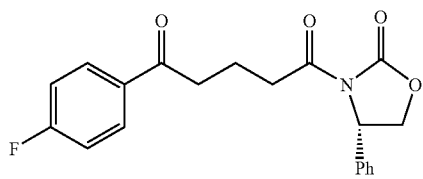

is reduced by sodium borohydride, chlorotrimethylsilane and optically active 2-[bis(4-methoxyphenyl)hydroxymethyl] pyrrolidine represented by formula (IV)

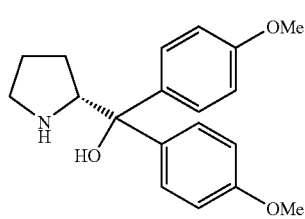

to give 3-[(5S)-(4-fluorophenyl)-5-hydroxypentanoyl]-(4S)-phenyl-1,3-oxazolidin-2-one represented by formula (VII) stereoselectively.

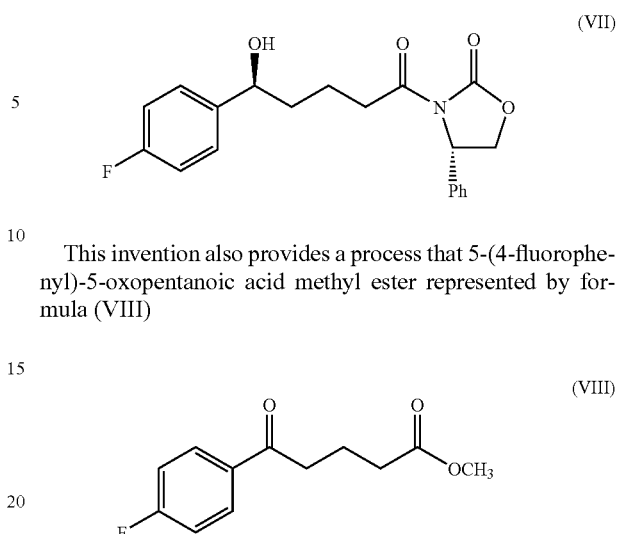

This invention also provides a process that 5-(4-fluorophenyl)-5-oxopentanoic acid methyl ester represented by formula (VIII)

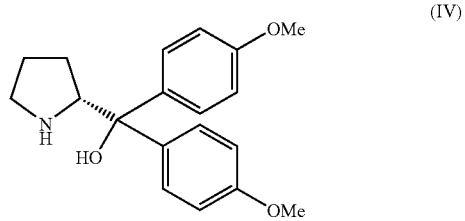

is reduced by sodium borohydride, chlorotrimethylsilane and optically active 2-[bis(4-methoxyphenyl)hydroxymethyl] pyrrolidine represented by formula (IV)

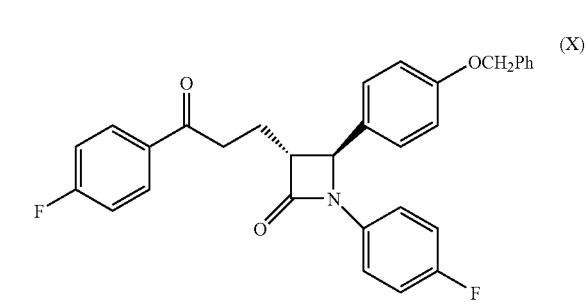

to give (5S)-(4-fluorophenyl)-5-oxopentanoic acid methyl ester represented by formula (IX) stereoselectively.

This invention also provides a process in which (4S)-(4-benzyloxyphenyl)-1-(4-fluorophenyl)-(3R)-[3-(4-fluorophenyl)-3oxopropyl]azetidin-2-one represented by formula (X)

is reduced by sodium borohydride, chlorotrimethylsilane and optically active 2-[bis(4-methoxyphenyl)hydroxymethyl]pyrrolidine represented by formula (IV)

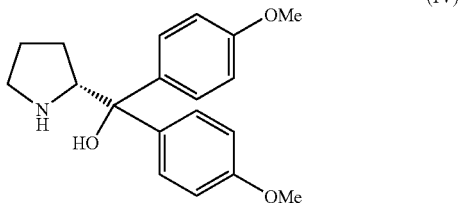

(IV)

to give (4S)-(4-benzyloxyphenyl)-1-(4-fluorophenyl)-(3R)-[(3S)-(4-fluorophenyl)-3-oxopropyl]azetidin-2-one represented by formula (IX) stereoselectively.

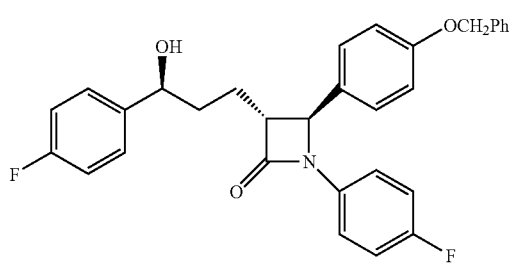

(XI)

BEST MODE FOR CARRYING OUT THE INVENTION

Compounds represented by general formula (I) are defined herein. $R^1$ is selected from a hydrogen atom, halogen atom (e.g. fluorine atom, chlorine atom, bromine atom, iodine atom), alkyl group (e.g. methyl group, ethyl group, propyl group, butyl group, pentyl group, haloalkyl group (e.g. trifluoromethyl group, 2,2,2,-trifluoroethyl group), alkoxycarbonyl group (e.g. methylxycarbonyl group, ethoxycarbonyl group, propyloxycarbonyl group, butoxycarbonyl group, pentyloxycarbonyl group), alkoxy group (e.g. methoxy group, ethoxy group, propyloxy group, butoxy group, pentyloxy group), hydroxyl group, nitro group, cyano group, acyloxy group (e.g. acetyloxy group, propionyloxy group), alkylthio group (e.g. methylthio group, ethylthio group, propylthio group, butylthio group, pentylthio group), alkylsulfonyl group (e.g. methylsulfonyl group, ethylsulfonyl group, propylsulfonyl group, butylsulfonyl group, pentylsulfonyl group), substituted or unsubstituted amino group (e.g. amino group, methylamino group, ethylamino group, propylamino group, butylamino group, pentylamino group, dimethylamino group, diethylamino group, dipropylamino group, dibutylamino group, dipentylamino group, acetylamino group, propionylamino group, methoxycarbonylamino group, ethoxycarbonylamino group, propionylcarbonylamino group, butoxycarbonylamino group, pentyloxycarbonylamino group, methylsulfonylamino group, ethylsulfonylamino group), substituted or unsubstituted carbamoyl group (e.g. carbamoyl group, methylaminocarbonyl group, ethylaminocarbonyl group, propylaminocarbonyl group, butylaminocarbonyl group, pentylaminocarbonyl group, dimethylamino group, diethylamino group, diethylaminocarbonyl group, dipropylaminocarbonyl group, dibutylaminocarbonyl group, dipentylaminocarbonyl group), substituted or unsubstituted aromatic ring (e.g. phenyl group, fluorophenyl group, chlorophenyl group, bromophenyl group, iodophenyl group, methylphenyl group, methoxyphenyl group, aminophenyl group, cyanophenyl group, methylthiophenyl group, methylsulfamoylphenyl group, methylsulfonylphenyl group, naphtyl group, azulenyl group, biphenyl group, phenoxyphenyl group) or heteroaromatic ring (e.g. pyridine ring, furan ring, thiophene ring, imidazole ring, thiazole ring, benzofuran ring, benzothiophene ring, benzimidazole ring, benzothiazole ring).

$R^2$ is selected from an alkyl group (e.g. methyl group, ethyl group, propyl group, butyl group, pentyl group), haloalkyl group (e.g. chloromethyl group, 2-chloroethyl group, 3-chloropropyl group, 4-chlorobutyl group, 5-chloropentyl group, bromomethyl group, 2-bromoethyl group, 3-bromopropyl group, 4-bromobutyl group, 5-bromopentyl group, iodomethyl group, 2-iodoethyl group, 3-iodopropyl group, 4-iodobutyl group, 5-iodopentyl group), alkyl group containing a methoxycarbonyl group (e.g. methoxycarbonylmethyl group, 2-methoxycarbonylethyl group, 3-methoxycarbonylpropyl group, 4-methoxycarbonylbutyl group, 5-methoxycarbonylpentyl group, 3-ethoxycarbonylpropyl group, 3-propyloxycarbonylpropyl group, 3-butoxycarbonylpropyl group, 3-pentyloxycarbonylpropyl group), alkyl group containing an alkoxy group (e.g. methoxymethyl group, 2-methoxyethyl group, 3-methoxypropyl group, 4-methoxybutyl group, 5-methoxypentyl group, 4-ethoxybutyl group, 4-propyloxybutyl group, 4-butoxybutyl group, 4-pentyloxybutyl group), hydroxyl group, alkyl group containing an alkylthio group (e.g. methylthiomethyl group, 2-methylthioethyl group, 3-methylthiopropyl group, 4-methylthiobutyl group, 5-methylthiopenty group, 4-ethylthiobutyl group, 4-propylthiobutyl group, 4-pentylthiobutyl group), alkyl group containing an alkylsulfonyl group (e.g. methylsulfonylmethyl group, 2-methylsulfonylethyl group, 3-methylsulfonylpropyl group, 4-methylsulfonylbutyl group, 5-methylsulfonylpentyl group, 4-ethylsulfonylbutyl group, 4-propylsulfonylbutyl group, 4-butylsulfonylbutyl group, 4-pentylsulfonylbutyl group), alkyl group containing a substituted or unsubstituted amino group (e.g. dimethylaminomethyl group, 2-dimethylaminoethyl group, 3-dimethylaminopropyl group, 4-dimethylaminobutyl group, 5-dimethylaminopentyl group, 4-diethylaminobutyl group, 4-dipropylaminobutyl group, 5-dipentylaminobutyl group, acetylaminomethyl group, 2-acetylaminoethyl group, 3-acetylaminopropyl group, 4-acetylaminobutyl group, 5-acetylaminopentyl group, 4-propionylaminobutyl group, methoxycarbonylaminomethyl group, 2-methoxycarbonylaminoethyl group, 3-methoxycarbonylaminopropyl group, 4-methoxycarbonylaminobutyl group, 5-methoxycarbonylaminopentyl group, 4-ethoxycarbonylaminobutyl group, 4-propyloxycarbonylaminobutyl group, 4-butoxycarbonylaminobuty group, 4-pentyloxycarbonylaminobutyl group, methylsulfonylaminomethyl group, 2-methylsulfonylaminoethyl group, 3-methylsulfonylaminopropyl group, 4-methylsulfonylaminobutyl group, 5-methylsulfonylaminopentyl group, 4-ethylsulfonylaminobutyl group, 4-propylsulfonylaminobutyl group, 4-butylsulfonylaminobutyl group, 4-pentylsulfonylaminobutyl group), alkyl group containing a substituted or unsubstituted carbamoyl group (e.g. carbamoylmethyl group, 2-carbamoylethyl group, 3-carbamoylpropyl group, 4-carbamoylbutyl group, 5-carbamoylpentyl group, 3-methylaminocarbonylpropyl group, 3-dimethylaminocarbamoylpropyl group, 3-ethylaminocarbonylpropyl group, 3-diethylaminocarbonylpropyl group, 3-propylaminocarbonylpropyl group, 3-dipropylaminocarbonylpropyl group, 3-butylaminocarbonylpropyl group, 3-propylaminocarbonylpropyl group, 3-butylaminocarbonylpropyl group, 3-dibutylaminocarbonylpropyl group, 3-pentylaminocarbonylpropyl group, 3-dipentylaminocarbonylpropyl group), alkyl group containing a substituted or unsubstituted aromatic ring (e.g. benzyl group, 2-phenylethyl group, 3-phenylpropyl group, 4-phenylbutyl group, 5-phenylpentyl group, 4-(fluorophenyl)butyl group, 4-(chlorophenyl)butyl group, 4-(bromophenyl)butyl group, 4-(iodophenyl)butyl group, 4-(methylphenyl)butyl group, 4-(methoxyphenyl)butyl group, 4-(aminophenyl)butyl group, 4-(cyanophenyl)butyl group, 4-(methylthiphenyl)butyl group, 4-(methylsulfonylphenyl)butyl group, 4-(naphtyl)phenyl, 4-(azulenyl)butyl group), alkyl group containing a substituted or unsubstituted heteroaromatic ring (e.g. 4-(pyridyl)butyl group, 4-(furyl) butyl group, 4-(thiophenyl)butyl group, 4-(imidazolyl)butyl group, 4-(thiazolyl)butyl group, 4-(benzofuryl)butyl group, 4-(benzothiophenyl)butyl group, 4-(benzoimidazolyl) butyl group, 4-(benzothiazolyl)butyl group) and formula (XVII)

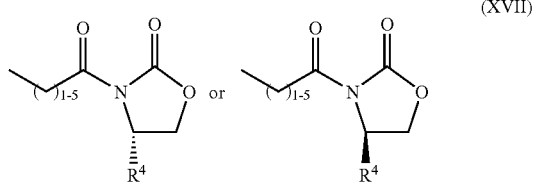

(XVII)

and formula (XVIII).

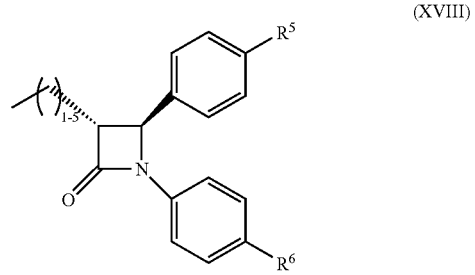

(XVIII)

$R^4$ is selected from an alkyl group (e.g. methyl group, ethyl group, propyl group, butyl group, isobutyl group, t-butyl group, pentyl group), substituted or unsubstituted aromatic ring (e.g. phenyl group, fluorophenyl group, chlorophenyl group, bromophenyl group, iodophenyl group, methylphenyl group, methoxyphenyl group, aminophenyl group, cyanophenyl group, methylthiphenyl group, methylsulfonylphenyl group, naphtyl group, azulenyl group, biphenyl group, phenoxyphenyl group), substituted or unsubstituted benzyl group (e.g. benzyl group, fluorobenzyl group, chlorobenzyl group, bromobenzyl group, iodobenzyl group, methylbenzyl group, methoxybenzyl group, aminobenzyl group, cyanobenzyl group, methylthiobenzyl group, methylsulfonylbenzyl group, naphtylmethyl group, azulenylmethyl group, biphenylmethyl group, phenoxybenzyl group).

$R^5$ and $R^6$ are the same or different and are selected from a hydrogen atom, halogen atom (e.g. fluorine atom, chlorine atom, bromine atom, iodine atom), alkyl group (e.g. methyl group, ethyl group, propyl group, butyl group, pentyl group), haloalkyl group (e.g. trifluoromethyl group, 2,2,2-trifluoroethyl group, chloromethyl group, bromomethyl group, iodomethyl group, 2-bromoethyl group, 3-bromopropyl group, 4-bromobutyl group, 5-bromopentyl group,), lower alkoxycarbonyl group (e.g. methylxycarbonyl group, ethoxycarbonyl group, propyloxycarbonyl group, butoxycarbonyl group, pentyloxycarbonyl group), lower alkoxy group (e.g. methoxy group, ethoxy group, propyloxy group, butoxy group, pentyloxy group), lower acyloxy group (acetyloxy group, propionyloxy group), hydroxyl group, nitro group, cyano group, substituted or unsubstituted benzyloxy group (e.g. benzyloxy group, fluorobenzyloxy group, chlorobenzyloxy group, bromobenzyloxy group, iodobenzyloxy group, methylbenzyloxy group, methoxybenzyloxy group, aminobenzyloxy group, cyanobenzyloxy group, methylthiobenzyloxy group, methylsulfonylbenzyloxy group, naphtylmethyloxy group, azulenylmethyloxy group, biphenylmethyloxy group, phenoxybenzyloxy group), substituted silyl group (e.g. trimethylsilyl group, triethylsilyl group, triisopropylsilyl group, t-butyldimethylsilyl group, t-butyldiphenylsilyl group), alkylthio group (e.g. methylthio group, ethylthio group, propylthio group, butylthio group, pentylthio group), alkylsulfonyl group (e.g. methylsulfonyl group, ethylsulfonyl group, propylsulfonyl group, butylsulfonyl group, pentylsulfonyl group), substituted or unsubstituted amino group (e.g. amino group, methylamino group, ethylamino group, propylamino group, butylamino group, pentylamino group, dimethylamino group, diethylamino group, dipropylamino group, dibutylamino group, dipentylamino group, acetylamino group, propionylamino group, methoxycarbonylamino group, ethoxycarbonylamino group, propionylcarbonylamino group, butoxycarbonylamino group, pentyloxycarbonylamino group, methylsulfonylamino group, ethylsulfonylamino group), substituted or unsubstituted carbamoyl group (e.g. carbamoyl group, methylaminocarbonyl group, ethylaminocarbonyl group, propylaminocarbonyl group, butylaminocarbonyl group, pentylaminocarbonyl group, dimethylamino group, diethylamino group, diethylaminocarbonyl group, dipropylaminocarbonyl group, dibutylaminocarbonyl group, dipentylaminocarbonyl group), substituted or unsubstituted aromatic ring (e.g. phenyl group, fluorophenyl group, chlorophenyl group, bromophenyl group, iodophenyl group, methylphenyl group, methoxyphenyl group, aminophenyl group, cyanophenyl group, methylthiphenyl group, methylsulfamoylphenyl group, methylsulfonylphenyl group, naphtyl group, azulenyl group, biphenyl group, phenoxyphenyl group), or heteroaromatic ring (e.g. pyridine ring, furan ring, thiophene ring, imidazole ring, thiazole ring, benzofuran ring, benzothiophene ring, benzimidazole ring, benzothiazole ring), substituted or unsubstituted tetrahydropyranyl group (e.g. tetrahydropyranyl group, fluorotetrahydropyranyl group, chlorotetrahydropyranyl group, methyltetrahydropyranyl group, methoxytetrahydropyranyl group, hydroxytetrahydropyranyl group, acetoxytetrahydropyranyl group, benzyloxytetrahydropyranyl group, trimethylsilyloxytetrahydropyranyl group, methoxycarbonyltetrahydropyranyl group), alkyl group containing a substituted or unsubstituted tetrahydropyranyl group (tetrahydropyranylmethyl group, 2-tetrahydropyranylethyl group, 3-tetrahydropyranylpropyl group, 4-tetrahydropyranylbutyl group, 5-tetrahydropyranylpentyl group, 2-(fluorotetrahydropyranyl)ethyl group, 2-(chlorotetrahydropyranyl)ethyl group, 2-(methyltetrahydropyranyl)ethyl group, 2-(methoxytetrahydropyranyl)ethyl group, 2-(hydroxytetrahydropyranyl)ethyl group, 2-(acetoxytetrahydropyranyl)ethyl group, 2-(benzyloxytetrahydropyranyl)ethyl group, 2-(trimethylsilyloxytetrahydropyranyl)ethyl group, 2-(methoxycarbonyltetrahydropyranyl)ethyl group), alkyl group containing an amino group (e.g. dimethylaminomethyl group, 2-dimethylaminoethyl group, 3-dimethylaminopropyl group, 4-dimethylaminobutyl group, 5-dimethylaminopentyl group, 4-diethylaminobutyl group, 4-dipropylaminobutyl group, 5-dipentylaminopentyl group).

This invention is a process for producing optically active alcohols by asymmetric reduction of aromatic ketones represented by general formula (I) using sodium borohydride, chlorotrimethylsilane and optically active 2-[bis(4-methoxyphenyl)hydroxymethyl]pyrrolidine (IV). Optically active 2-[bis(4-methoxyphenyl)hydroxymethyl]pyrrolidine (IV), which is used in this invention, can be synthesized from D- or L-proline according to the literatures (Journal of Chemical Society, Perkin Trans 1, 1985, 2039; Journal of American Society, 1987, 109, 5551; Tetrahedron, 1993, 49, 5127; Synthesis, 2004, 217).

The reaction is carried out in one-pot according to the method described in Tetrahedron Letters (2000, 41, 10281). This reaction consists of 3 steps.

1 step: The reaction of sodium borohydride with chlorotrimethylsilane.

2 step: Preparation of an asymmetric reducing agent by the addition of optically active 2-[bis(4-methoxyphenyl)hydroxyl-methyl]pyrrolidine into the 1 step reaction mixture.

3 step: An aromatic ketone is reduced by addition into the 2 step reaction mixture to give an optically active alcohol.

1 step: The amount of sodium borohydride and chlorotrimethylsilene is 1 to 1.5-fold mol per aromatic ketone. Preferably, the amount is 1.2 to 1.4-fold mol. The reaction is carried out in an inert solvent such as an ethereal solvent (ether, isopropyl ether, t-butyl methyl ether, tetrahydrofuran, 1,4-dioxane) and a halogenated solvent (dichloromethane, 1,2-dichloroethane). Preferably, the reaction solvent is tetrahydrofuran. The reaction is carried out under a reflux temperature and reaction time is about 1 hr.

2 step: The mixture of sodium borohydride and chlorotrimethylsilane is reacted with 2-[bis(4-methoxyphenyl)hydroxymethyl]pyrrolidine by dropwise addition. The reaction is carried out at 0° C. to 40° C. and the reaction time is 0.5 hr. The amount of optically active 2-[bis(4-methoxyphenyl)hydroxymethyl]pyrrolidine is 5 mol % to 20 mol % per aromatic ketone. Preferably, the amount is 10 mol %.

3 step: An aromatic ketone is reduced by the asymmetric reducing agent prepared in the 1 and 2 steps. The aromatic ketone is added dropwise to the reaction mixture. The reduction is carried out at 0° C. to 40° C. Preferably, the reaction temperature is 15° C. to 30° C.

3-[5-(4-Fluorophenyl)-5-oxopentanoyl]-(4S)-phenyl-1,3-oxazolidin-2-one (VI) and 5-(4-fluorophenyl)-5-oxopentanoic acid methyl ester (VIII) can be prepared in accordance with the procedure in U.S. Pat. No. 6,207,822.

(4S)-(4-Benzyloxyphenyl)-1-(4-fluorophenyl)-(3R)-[3-(4-fluorophenyl)-3-oxopropyl]azetidin-2-one (X) can be synthesized as described in Journal of Organic Chemistry, 1999, 64, 3714 or Journal of Medicinal Chemistry, 1998, 41, 973.

3-[(5S)-(4-Fluorophenyl)-5-hydroxypentanoyl]-(4S)-phenyl-1,3-oxazolidin-2-one (VII), which is obtained by the asymmetric reduction of 3-[5-(4-fluorophenyl)-5-oxopentanoyl]-(4S)-phenyl-1,3-oxazolidin-2-one (VI), is available to produce ezetimibe by the β-lactam ring construction.

On the other hand, (5S)-(4-fluorophenyl)-5-hydroxypentanoic acid methyl ester (IX), which is obtained by the asymmetric reduction of 5-(4-fluorophenyl)-5-oxopentanoic acid methyl ester (VIII), is utilized to produce 3-[(5S)-(4-fluorophenyl)-5-hydroxypentanoyl]-(4S)-phenyl-1,3-oxazolidin-2-one (VII). Furthermore, (4S)-(4-benzyloxyphenyl)-1-(4-fluorophenyl)-(3R)-[(3S)-(4-fluorophenyl)-3-hydroxypropyl]azetidin-2-one (XI), which is obtained by the asymmetric reduction of (4S)-(4-benzyloxyphenyl)-1-(4-fluorophenyl)-(3R)-[3-(4-fluorophenyl)-3-oxopropyl]azetidin-2-one (X), is available to produce ezetimibe.

Example 1

Preparation of 3-[(5S)-(4-fluorophenyl)-5-hydroxypentanoyl]-(4S)-phenyl-1,3-oxazolidin-2-one Chlorotrimethylsilane (25.0 mL, 0.197 mol) was added to a suspension of sodium borohydride (7.45 g, 0.197 mol) in tetrahydrofuran (700.0 mL) at 24° C., and the reaction mixture was stirred under reflux for 1 hr. The reaction mixture was cooled to 24° C., and a solution of (R)-2-[bis(4-methoxyphenyl)hydroxymethyl]pyrrolidine (4.41 g, 0.014 mol) in tetrahydrofuran (280.0 mL) was added. After stirring for 0.5 hr, a solution of 3-[5-(4-fluorophenyl)-5-oxopentanoyl]-(4S)-phenyl-1,3-oxazolidin-2-one (50.00 g, 0.141 mol) in tetrahydrofuran (280.0 mL) was added dropwise for 80 min. After stirring for 10 min, the reaction mixture was cooled to 4° C. 6N-HCl was added to the reaction mixture, and water and toluene were added. After stirring for 30 min, the organic layer was separated. The organic layer was washed with water, aqueous saturated sodium bicarbonate and aqueous saturated sodium chloride, and dried over sodium sulfate. Filtration and evaporation gave 3-[(5S)-(4-fluorophenyl)-5-hydroxypentanoyl]-(4S)-phenyl-1,3-oxazolidin-2-one 48.71 g as a colorless oil.

$^1$H-NMR (CDCl$_3$) δ=1.56-1.75 (m, 4H), 1.97 (d, J=3 Hz, 1H), 2.96-2.99 (m, 2H), 4.28 (dd, J=3 Hz, 9 Hz, 1H), 4.56-4.66 (m, 1H), 4.68 (t, J=9 Hz, 1H), 5.40 (dd, J=3 Hz, 9 Hz, 1H), 6.98-7.02 (m, 2H), 7.25-7.37 (m, 7H).

The de, diastereoselectivity de (%)=[(S,S) %-(R,R) %], of the desired product was determined to be 93% by HPLC using a chiral column. (column: CHIRALCELL OD-H® of DAICEL, mobile phase: ethanol/n-hexane=1/5 (v/v), detection: UV at 258 nm).

Example 2

The loading amount (mol %) of (R)-2-[bis(4-methoxyphenyl)hydroxymethyl]pyrrolidine and the reaction scale of 3-[5-(4-fluorophenyl)-5-oxopentanoyl]-(4S)-phenyl-1,3-oxazolidin-2-one (VI) were changed as shown in Table 1, and 3-[(5S)-(4-fluorophenyl)-5-hydroxypentanoyl]-(4S)-phenyl-1,3-oxazolidin-2-one was synthesized using the general procedure of Example 1 above. The de (%) of the desired product was determined by HPLC using a chiral column. The results are summarized in Table 1.

In the reduction using 3-[5-(4-fluorophenyl)-5-oxopentanoyl]-(4S)-phenyl-1,3-oxazolidin-2-one as a catalyst, (R)-2-[bis(4-methoxyphenyl)hydroxymethyl]pyrrolidine was replaced with (R)-2-(diphenylhydroxymethyl)pyrrolidine in order to compare the de of the resulting product. As shown in Table 1, the loading amount (mol %) of (R)-2-(diphenylhydroxymethyl)pyrrolidine and the reaction scale of 3-[5-(4-fluorophenyl)-5-oxopentanoyl]-(4S)-phenyl-1,3-oxazolidin-2-one (VI) were changed. The de (%) of the desired product was determined by HPLC using a chiral column. The results are summarized in Table 1.

In the reduction using 3-[5-(4-fluorophenyl)-5-oxopentanoyl]-(4S)-phenyl-1,3-oxazolidin-2-one as a catalyst, (R)-2-[bis(4-methoxyphenyl)hydroxymethyl]pyrrolidine was replaced with (R)-2-[bis(4-trifluorophenyl)hydroxymethyl]pyrrolidine in order to compare the de of the resulting product. The loading amount (mol %) of (R)-2-(diphenylhydroxymethyl)pyrrolidine and the reaction scale of 3-[5-(4-fluorophenyl)-5-oxopentanoyl]-(4S)-phenyl-1,3-oxazolidin-2-one (VI) were shown in Table 1. The de (%) of the desired product was determined by HPLC using a chiral column. The results are summarized in Table 1.

TABLE 1

| Pyrrolidine derivative | Amount of pyrrolidine derivative (mol %) | Reaction scale (compound VI, g) | de (%) [(S,S)% − (S,R)%] |
|---|---|---|---|
| (R)-2-[bis(4-methoxyphenyl)hydroxymethyl]pyrrolidine | 10 | 1 | 89 |
|  | 10 | 10 | 90 |
|  | 10 | 20 | 90 |
|  | 10 | 50 | 93 |
| (R)-2-(diphenylhydroxymethyl)pyrrolidine | 10 | 1 | 87 |
|  | 10 | 10 | 74 |
| (R)-2-[bis(4-trifluorophenyl)hydroxymethyl]pyrrolidine | 10 | 1 | 58 |

As shown in Table 1, when (R)-2-[bis(4-methoxyphenyl)hydroxymethyl]pyrrolidine is used as a catalyst during large scale production, the de of the reaction product increased. In the case of (R)-2-(diphenylhydroxymethyl)pyrrolidine, the de of the reaction product decreased during large scale production. When (R)-2-[bis(4-trifluorophenyl)hydroxymethyl] pyrrolidine was used as a catalyst, the de of the reaction product dramatically decreased during small scale production.

Example 3

Preparation of (5S)-(4-fluorophenyl)-5-hydroxypentanoic Acid Methyl Ester

Chlorotrimethylsilane (2.0 mL, 0.01606 mol) was added to a suspension of sodium borohydride (0.61 g, 0.01606 mol) in tetrahydrofuran (63.0 mL) at 20° C., and the reaction mixture was stirred under reflux for 1 hr. The reaction mixture was cooled to 24° C., and a solution of (R)-2-[bis(4-methoxyphenyl)hydroxylmethyl]pyrrolidine (0.42 g, 0.00134 mol) in tetrahydrofuran (10.0 mL) was added. After stirring for 0.5 hr, a solution of 5-(4-fluorophenyl)-5-oxopentanoic acid methyl ester (VIII) (3.00 g, 0.01338 mol) in tetrahydrofuran (10.0 mL) was added dropwise for 45 min. After stirring for 1.5 hr, the reaction mixture was cooled to 2° C. 6N-HCl was added dropwise to the reaction mixture, and water and ethyl acetate were added. After stirring for 30 min, the organic layer was separated. The organic layer was washed with water, aqueous saturated sodium bicarbonate and aqueous saturated sodium chloride, and dried over sodium sulfate. Filtration and evaporation gave the crude product, which was purified by silica gel column chromatography (ethyl acetate/n-hexane) to give (5S)-(4-fluorophenyl)-5-hydroxypentanoic acid methyl ester 2.79 g as a colorless oil.

$^1$H-NMR (CDCl$_3$) δ=1.59-1.80 (m, 4H), 2.21 (s, 1H), 2.32-2.36 (m, 2H), 3.65 (s, 3H), 4.63-4.68 (m, 1H), 7.00-7.04 (m, 2H), 7.26-7.32 (m, 2H).

The ee, enantioselectivity ee (%)=[(S) %−(R) %], of the desired product was determined by HPLC using a chiral column. (column: CHIRALPAK AD® of DAICEL, mobile phase: ethanol/n-hexane=1/20 (v/v), detection: UV at 258 nm). The result is shown in Table 2.

Comparative Example 1

Chlorotrimethylsilane (0.86 mL, 0.005352 mol) was added to a suspension of sodium borohydride (0.202 g, 0.005352 mol) in tetrahydrofuran (21.0 mL) at 21° C., and the reaction mixture was stirred under reflux for 1 hr. The reaction mixture was cooled to 24° C., and a solution of (R)-2-(diphenylhydroxymethyl)pyrrolidine (0.114 g, 0.0004466 mol) in tetrahydrofuran (5.0 mL) was added. After stirring for 0.5 hr, a solution of 5-(4-fluorophenyl)-5-oxopentanoic acid methyl ester (VIII) (1.00 g, 0.00446 mol) in tetrahydrofuran (5.0 mL) was added dropwise for 48 min. After stirring for 0.5 hr, the reaction mixture was cooled to 2° C. 6N-HCl was added dropwise to the reaction mixture, and water and ethyl acetate were added. After stirring for 30 min, the organic layer was separated. The organic layer was washed with water, aqueous saturated sodium bicarbonate and aqueous saturated sodium chloride, and dried over sodium sulfate. Filtration and evaporation gave the crude product, which was purified by silica gel column chromatography (ethyl acetate/n-hexane) to give 0.90 g of (5S)-(4-fluorophenyl)-5-hydroxypentanoic acid methyl ester as a colorless oil. The ee enantioselectivity ee (%)=[(S)%−(R)%] of the desired product was determined by HPLC using a chiral column. (column: CHIRALPAK AD® of DAICEL, mobile phase: ethanol/n-hexane=1/20 (v/v), detection: UV at 258 nm). The result is shown in Table 2.

TABLE 2

| Pyrrolidine derivative | Amount of pyrrolidine derivative (mol %) | Reaction scale (compound VII, g) | ee (%) [(S)%-(R)%] |
| --- | --- | --- | --- |
| (structure with OMe groups) | 10 | 3 | 75 |
| (structure with phenyl groups) | 10 | 1 | 57 |

As shown in Table 2, when (R)-2-[bis(4-methoxyphenyl)hydroxymethyl]pyrrolidine was used as a catalyst during large scale production, the ee was larger than with (R)-2-(diphenylhydroxymethyl)pyrrolidine.

Example 4

Preparation of (4S)-(4-benzyloxyphenyl)-1-(4-fluorophenyl)(3R)-[(3S)-(4-fluorophenyl)-3-hydroxypropyl]azetidin-2-one Chlorotrimethylsilane (0.33 mL, 0.02613 mol) was added to a suspension of sodium borohydride (0.099 g, 0.02613 mol) in tetrahydrofuran (15.1 mL) at 19° C., and the reaction mixture was stirred under reflux for 1 hr. The reaction mixture was cooled to 22° C. and a solution of (R)-2-[bis(4-methoxyphenyl)hydroxylmethyl]pyrrolidine (0.063 g, 0.000201 mol) in tetrahydrofuran (5.2 mL) was added. After stirring for 0.5 hr, a solution of (4S)-(4-benzyloxyphenyl)-1-(4-fluorophenyl)-(3R)-[3-(4-fluorophenyl)-3-oxopropyl]azetidin-2-one (1.00 g, 0.00201 mol) in tetrahydrofuran (5.2 mL) was added dropwise for 8 min. After stirring for 1 hr, the reaction mixture was cooled to 2° C. 6N-HCl was added dropwise to the reaction mixture, and water and toluene were added. After stirring for 30 min, the organic layer was separated. The organic layer was washed with water, aqueous saturated sodium bicarbonate and aqueous saturated sodium chloride, and dried over sodium sulfate. Filtration and evaporation gave the crude product, which was purified by silica gel column chromatography (ethyl acetate/n-hexane) (4S)-(4-benzyloxyphenyl)-1-(4-fluorophenyl)-(3R)-[(3S)-(4-fluorophenyl)-3-hydroxypropyl]azetidin-2-one 0.89 g as colorless crystals.

$^1$H-NMR (CDCl$_3$) δ=1.88-2.01 (m, 4H), 2.19 (d, J=4 Hz, 1H), 3.07 (dt, J=2 Hz, 8 Hz, 1H), 4.57 (d, J=2 Hz, 1H), 4.71-4.73 (m, 1H), 5.29 (s, 2H), 6.90-7.03 (m, 6H), 7.21-7.43 (m, 11H).

The ee, enantioselectivity ee (%)=[(S) %-(R) %], of the desired product was determined by HPLC using a chiral column. (column: CHIRALPAK AD® of DAICEL, mobile phase: ethanol/n-hexane=1/9 (v/v), detection: UV at 258 nm). The result is shown in Table 3.

Comparative Example 2

Chlorotrimethylsilane (0.33 mL, 0.02613 mol) was added to a suspension of sodium borohydride (0.099 g, 0.02613 mol) in tetrahydrofuran (15.1 mL) at 19° C., and the reaction mixture was stirred under reflux for 1 hr. The reaction mixture was cooled to 22° C., and a solution of 2-(diphenylhydroxymethyl)pyrrolidine (0.051 g, 0.000201 mol) in tetrahydrofuran (5.2 mL) was added. After stirring for 0.5 hr, a solution of (4S)-(4-benzyloxyphenyl)-1-(4-fluorophenyl)-(3R)-[3-(4-fluorophenyl)-oxopropyl]azetidin-2-one (1.00 g, 0.00201 mol) in tetrahydrofuran (5.2 mL) was added dropwise for 7 min. After stirring for 70 min, the reaction mixture was cooled to 2° C. 6N-HCl was added dropwise to the reaction mixture, and water and toluene were added. After stirring for 30 min, the organic layer was separated. The organic layer was washed with water, aqueous saturated sodium bicarbonate and aqueous saturated sodium chloride, and dried over sodium sulfate. Filtration and evaporation gave the crude product, which was purified by silica gel column chromatography (ethyl acetate/n-hexane) (4S)-(4-benzyloxyphenyl)-1-(4-fluorophenyl)-(3R)-[(3S)-(4-fluorophenyl)-3-hydroxypropyl]azetidin-2-one 0.92 g as colorless crystals.

$^1$H-NMR (CDCl$_3$) δ=1.88-2.01 (m, 4H), 2.19 (d, J=4 Hz, 1H), 3.07 (dt, J=2 Hz, 8 Hz, 1H), 4.57 (d, J=2 Hz, 1H), 4.71-4.73 (m, 1H), 5.29 (s, 2H), 6.90-7.03 (m, 6H), 7.21-7.43 (m, 11H).

The ee of the desired product was determined by HPLC using a chiral column. (column: CHIRALPAK AD° of DAICEL, mobile phase: ethanol/n-hexane=1/9 (v/v), detection: UV at 258 nm).

The result is shown in Table 3.

TABLE 3

| Pyrrolidine derivative | Amount of pyrrolidine derivative (mol %) | Reaction scale (compound X, g) | ee (%) [(S)% − (R)%] |
|---|---|---|---|
| (structure with OMe groups) | 10 | 1 | 90 |
| (diphenyl structure) | 10 | 1 | 44 |

As shown in Table 3, when (R)-2-[bis(4-methoxyphenyl)hydroxylmethyl]pyrrolidine was used as a catalyst during the same scale production, the ee was about 2-fold larger than (R)-2-(diphenylhydroxymethyl)pyrrolidine.

Field of Industrial Application

Aromatic ketones are reduced to optically active alcohols in a high enantioselectivity by using the reduction process in this invention during large scale production. This invention is useful for producing optically active alcohols such as ezetimibe: ([1-(4-fluorophenyl)-(3R)-[3-(4-fluorophenyl)-(3S)-hydroxypropyl]-(4S)-(4-hydroxyphenyl)azetidin-2-one]), which is useful as a hypocholesterolemic agent in the prevention and treatment of atherosclerosis. The advantage of this process is that (R)-2-[(bis(4-methoxyphenyl)hydroxymethyl]pyrrolidine is recovered in a high yield at the reaction end-point by a simple operation such as extraction, and recyclable after a purification such as recrystallization. Furthermore, this reaction proceeds at room temperature and does not require a low reaction temperature.

The invention claimed is:

1. A process for producing an optically active alcohol of formula (V)

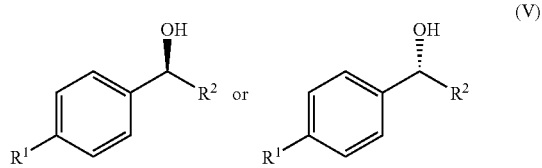

comprising the steps of reducing an aromatic ketone represented by formula (I), (II) or (III), (I)

(structure)

wherein $R^1$ is selected from a hydrogen atom, halogen atom, lower alkyl group having 1 to 5 carbon atoms, lower haloalkyl group having 1 to 5 carbon atoms, lower alkoxycarbonyl group having 1 to 5 carbon atoms, lower alkoxy group having 1 to 5 carbon atoms, hydroxyl group, nitro group, cyano group, lower acyloxy group having 1 to 5 carbon atoms, lower alkylthio group having 1 to 5 carbon atoms, lower alkylsulfonyl group having 1 to 5 carbon atoms, substituted and unsubstituted amino group, substituted and unsubstituted carbamoyl group, substituted and unsubstituted aromatic ring or heterocyclic group, $R^2$ is —$(CH_2)n$-$R^3$ wherein n is an integer of from 1 to 5, $R^3$ is selected from a hydrogen atom, halogen atom, lower alkoxycarbonyl group having from 1 to 5 carbon atoms, lower alkoxy group having from 1 to 5 carbon atoms, lower alkylthio group having from 1 to 5 carbon atoms, lower alkylsulfonyl group having from 1 to 5 carbon atoms, substituted and unsubstituted amino group, unsubstituted carbamoyl group, substituted and unsubstituted aromatic ring or heteroaromatic ring, formula (II)

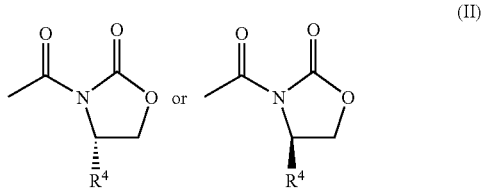

wherein $R^4$ is a lower alkyl group having from 1 to 5 carbon atoms, substituted and unsubstituted aromatic ring, and substituted and unsubstituted benzyl group, and formula (III):

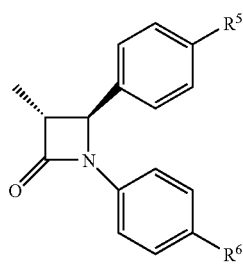
(III)

wherein $R^5$ and $R^6$ are the same or different and are selected from a hydrogen atom, halogen atom, lower alkyl group having 1 to 5 carbon atoms, lower haloalkyl group having 1 to 5 carbon atoms, lower alkoxycarbonyl group having 1 to 5 carbon atoms, lower alkoxy group having 1 to 5 carbon atoms, lower acyloxy group having 1 to 5 carbon atoms, hydroxyl group, nitro group, cyano group, substituted and unsubstituted benzyloxy group, substituted silyloxy group, lower alkylthio group having 1 to 5 carbon atoms, lower alkylsulfonyl group having 1 to 5 carbon atoms, substituted and unsubstituted amino group, substituted and unsubstituted carbamoyl group, substituted and unsubstituted aromatic ring or heteroaromatic ring, substituted and unsubstituted tetrahydropyranyl group, lower alkyl group containing a substituted or unsubstituted tetrahydropyranyl group having 1 to 5 carbon atoms, lower alkyl group containing an amino group having 1 to 5 carbon atoms, by sodium borohydride, chlorotrimethylsilane and an optically active 2-[bis(4-methoxyphenyl)hydroxy-methyl]pyrrolidine represented by formula (IV)

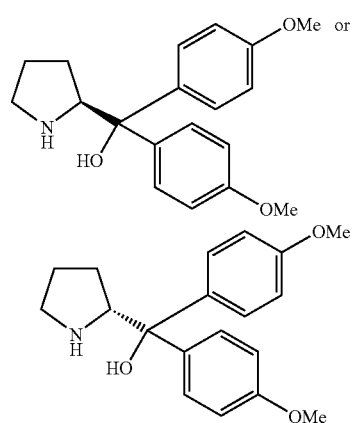
(IV)

to give the optically active alcohol.

2. The process of claim 1, wherein 3-[5-(4-fluorophenyl)-5-oxopentanoyl]-(4S)-phenyl-1,3-oxazolidin-2-one represented by formula (VI)

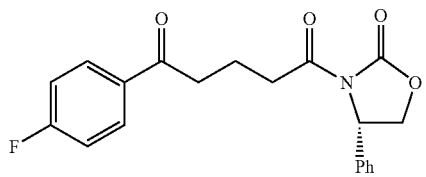
(VI)

is reduced by sodium borohydride, chlorotrimethylsilane and optically active (R)-2-[bis(4-methoxyphenyl)hydroxylmethyl]pyrrolidine represented by formula (IV)

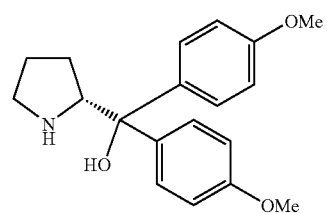
(IV)

to give 3-[(5S)-(4-fluorophenyl)-5-hydroxypentanoyl]-(4S)-phenyl-1,3-oxazolidin-2-one represented by formula (VII) stereoselectively

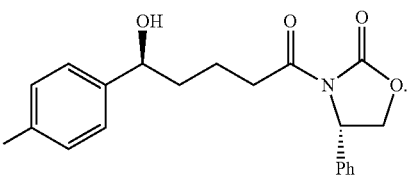
(VII)

3. The process of claim 1, wherein 5-(4-fluorophenyl)-5-oxopentanoic acid methyl ester represented by formula (VIII)

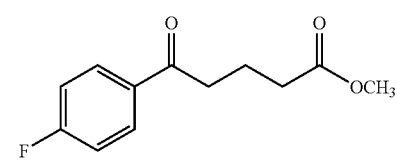
(VIII)

is reduced by sodium borohydride, chlorotrimethylsilane and optically active (R)-2-[bis(4-methoxyphenyl)hydroxylmethyl]pyrrolidine represented by formula (IV)

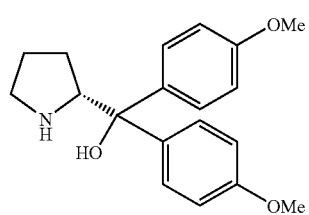
(IV)

to give (5S)-(4-fluorophenyl)-5-oxopentanoic acid methyl ester represented by formula (IX)

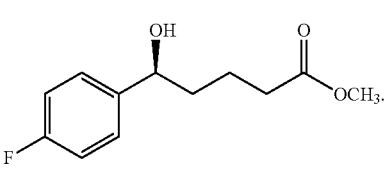
(IX)

4. The process of claim 1, wherein (4S)-(4-benzyloxyphenyl)-1-(4-fluorophenyl)-(3R)-[3-(4-fluorophenyl)-3-oxopropyl]azetidin-2-one represented by formula (X)

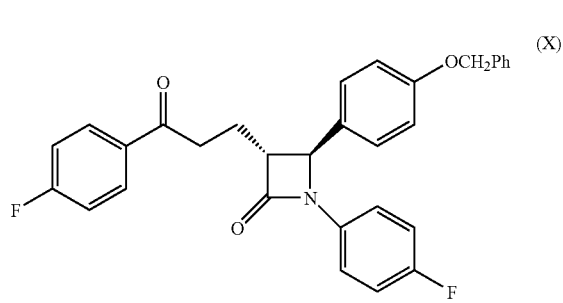
is reduced by sodium borohydride, chlorotrimethylsilane and optically active (R)-2-[bis(4-methoxyphenyl)hydroxymethyl]pyrrolidine represented by formula (IV)
to give (4S)-(4-benzyloxyphenyl)-1-(4-fluorophenyl)-(3R)-[(3S)-(4-fluorophenyl)-3 (S)-3-hydroxypropyl]azetidin-2-one represented by formula (XI)
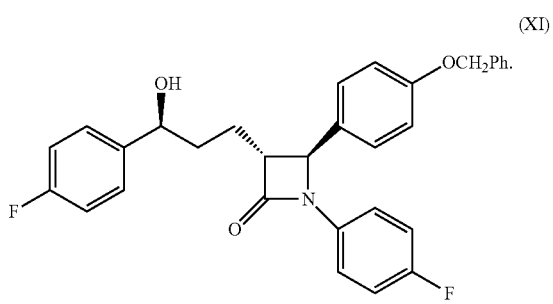
* * * * *